United States Patent
Kilpela et al.

(10) Patent No.: US 6,832,532 B2
(45) Date of Patent: Dec. 21, 2004

(54) MULTIPLE LUMEN CRIMP

(75) Inventors: Thomas S. Kilpela, Marquette, MI (US); Greg A. Berrevoets, Skandia, MI (US)

(73) Assignee: Pioneer Laboratories, Marquette, MI (US)

( * ) Notice: Subject to any disclaimer, the term of this patent is extended or adjusted under 35 U.S.C. 154(b) by 0 days.

(21) Appl. No.: 10/071,679

(22) Filed: Feb. 8, 2002

(65) Prior Publication Data

US 2002/0120282 A1 Aug. 29, 2002

Related U.S. Application Data

(62) Division of application No. 09/467,436, filed on Dec. 20, 1999, now Pat. No. 6,629,975.

(51) Int. Cl.[7] ................................................. B25B 7/14
(52) U.S. Cl. .............................. 81/315; 81/329; 81/338
(58) Field of Search ........................ 81/329, 338, 315, 81/424.5, 426, 426.5; 72/409.13, 409.14, 412, 416; 606/74, 113, 205

(56) References Cited

U.S. PATENT DOCUMENTS

| | | | | |
|---|---|---|---|---|
| 1,978,543 A | * | 10/1934 | Madeira | 29/227 |
| 2,461,030 A | | 2/1949 | Brickman | |
| 3,406,558 A | * | 10/1968 | Tillmann et al. | 72/416 |
| 3,802,438 A | | 4/1974 | Wolvek | |
| 4,269,180 A | | 5/1981 | Dall et al. | |
| 4,353,240 A | * | 10/1982 | Undin et al. | 72/409.12 |
| 4,541,312 A | * | 9/1985 | Petersen | 81/367 |
| 4,643,054 A | * | 2/1987 | Nelson | 81/352 |
| 4,966,600 A | | 10/1990 | Songer et al. | |
| 5,116,340 A | | 5/1992 | Songer et al. | |
| 5,335,531 A | * | 8/1994 | Mann et al. | 72/416 |
| 5,415,658 A | | 5/1995 | Kilpela et al. | |
| 5,496,341 A | * | 3/1996 | Sauer et al. | 606/167 |
| 5,536,270 A | * | 7/1996 | Songer et al. | 606/74 |
| 5,545,168 A | * | 8/1996 | Burke | 606/74 |
| 5,649,927 A | | 7/1997 | Kilpela et al. | |
| 5,741,260 A | * | 4/1998 | Songer et al. | 606/74 |
| 5,797,915 A | | 8/1998 | Pierson, III et al. | |
| 5,797,958 A | * | 8/1998 | Yoon | 606/207 |
| 5,941,881 A | | 8/1999 | Barnes | |
| 5,951,587 A | * | 9/1999 | Qureshi et al. | 606/207 |
| 6,017,347 A | | 1/2000 | Huebner et al. | |
| 6,120,505 A | | 9/2000 | Huebner | |
| 6,227,030 B1 | * | 5/2001 | Lefavour et al. | 72/416 |
| 6,457,338 B1 | * | 10/2002 | Frenken | 72/20.1 |
| 2002/0183785 A1 | * | 12/2002 | Howell et al. | 606/207 |

OTHER PUBLICATIONS

Howmedica Brochure; The Dall–Miles Trochanter Cable Grip System, date unknown.

* cited by examiner

Primary Examiner—Glenn K. Dawson
Assistant Examiner—Darwin Erezo
(74) Attorney, Agent, or Firm—Garrettson Ellis Seyfarth Shaw LLP

(57) ABSTRACT

A crimp defines separate parallel bores extending therethrough to receive a wire or cable portion. The crimp has a pair of opposed ends which each define a pair of circumferentially-spaced, outwardly projecting flanges respectively positioned on opposite sides of the crimp. Thus, the flanges may rest against a bone while providing spacing for crimping jaws between a central portion of the crimp and the bone. A design of crimping pliers for use with the crimp is also disclosed.

13 Claims, 5 Drawing Sheets

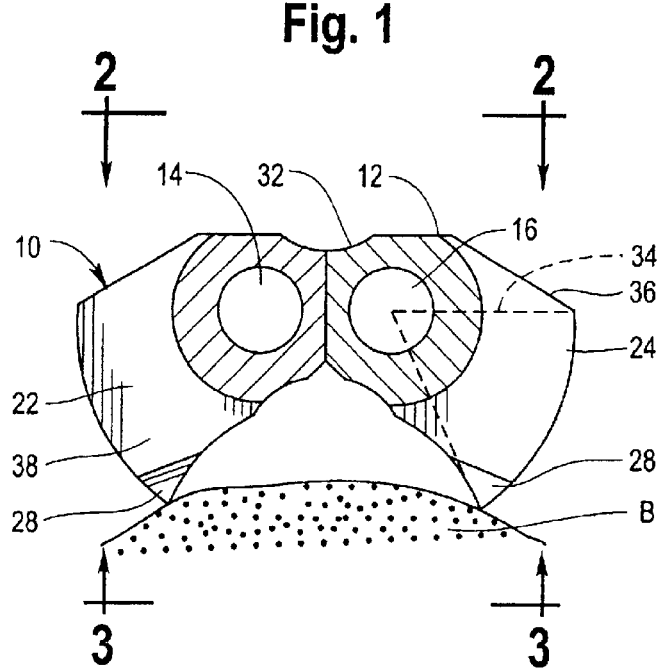
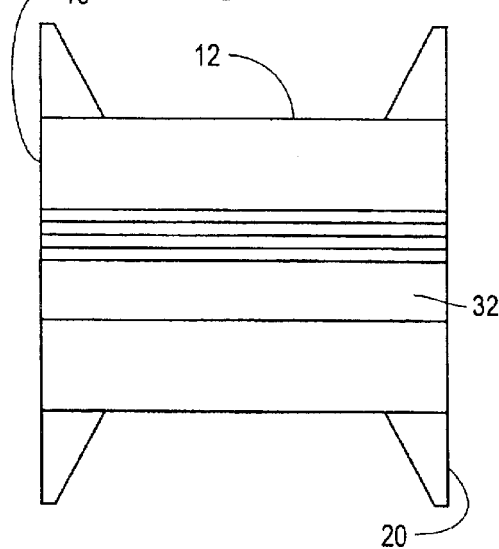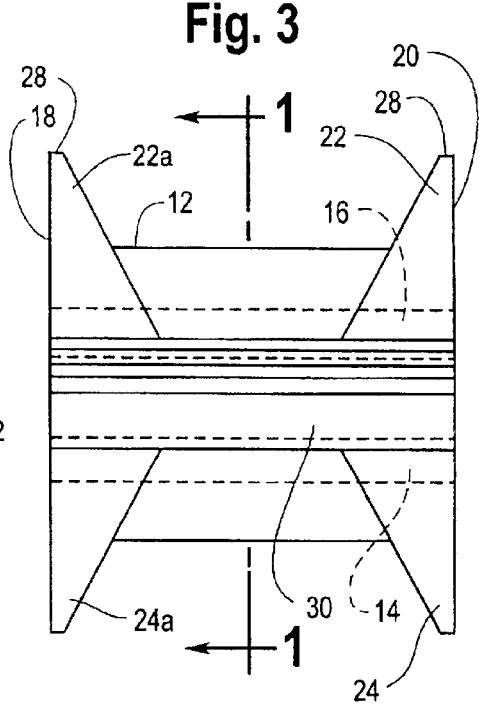

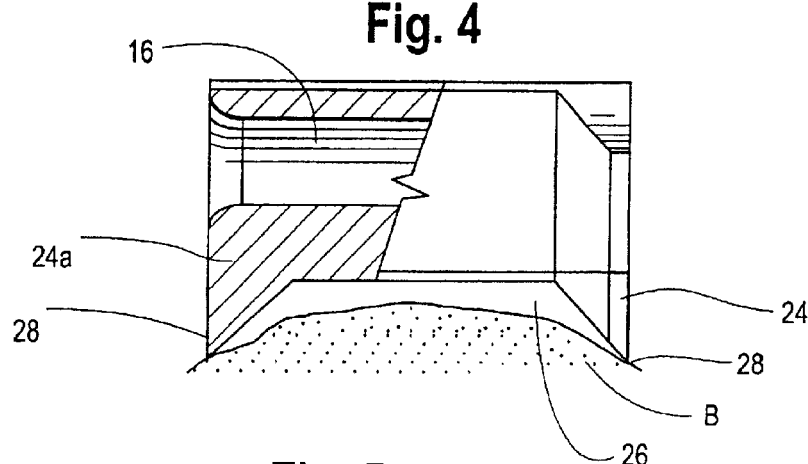
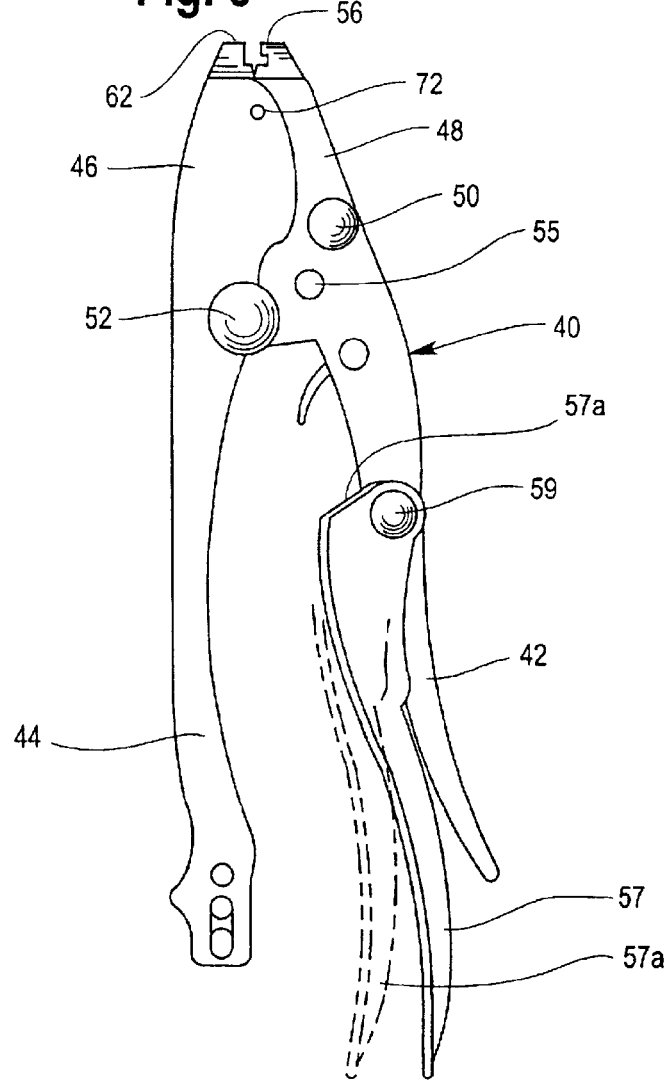

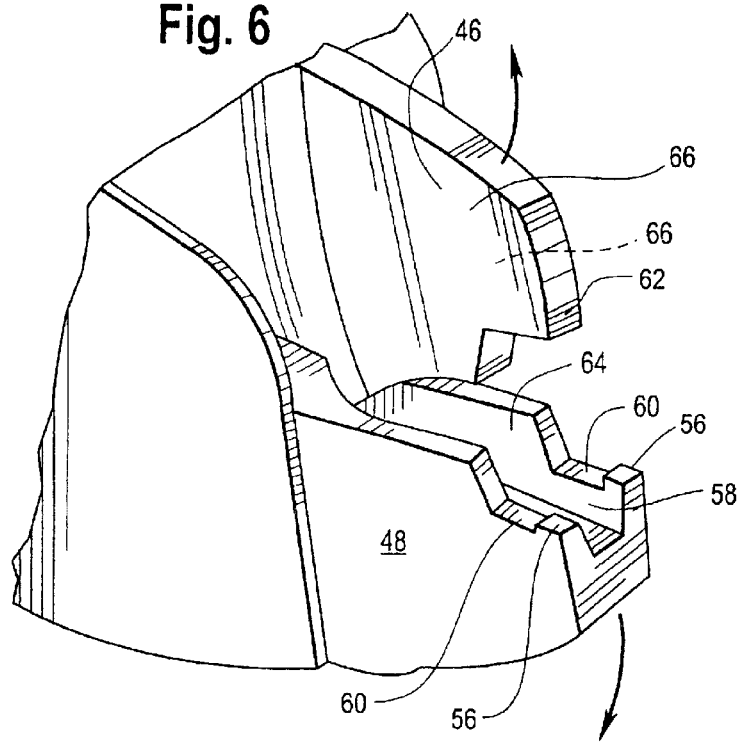
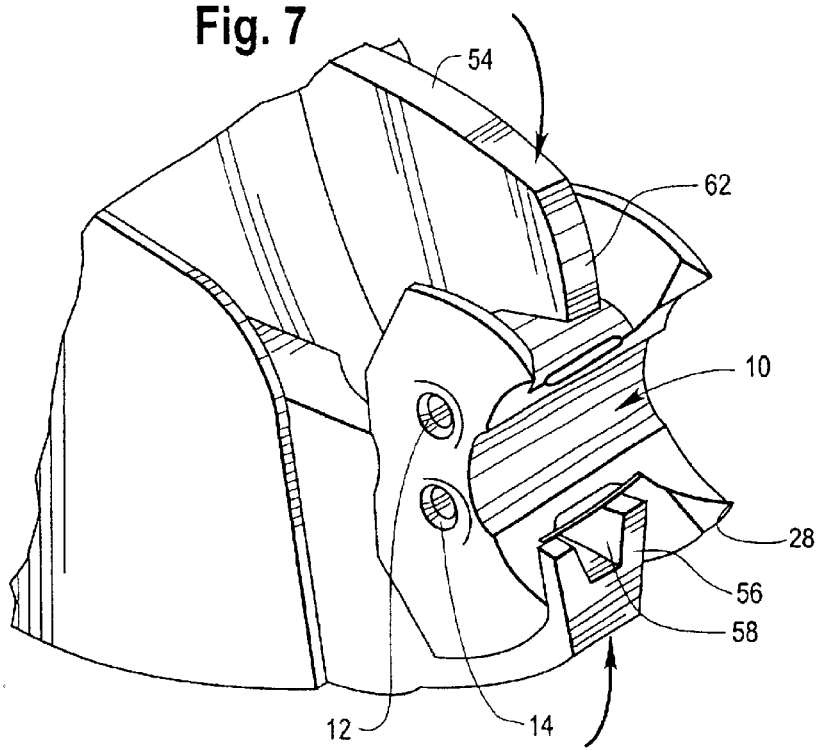

MULTIPLE LUMEN CRIMP

This is a divisional application of Ser. No. 09/467,436, filed Dec. 20, 1999 now U.S. Pat. No. 6,629,975.

BACKGROUND OF THE INVENTION

Surgically implanted orthopedic cables are for the purpose of retaining and positioning bones and bone portions within a patient to support the bones in a desired position and to permit healing to take place following surgery. Such surgical cables and wires are generally connected together by a crimp, which is crushable by crimping pliers for crimp retention. See for example, Songer et al. U.S. Pat. Nos. 4,966,600; 5,116,340; 5,536,270; and Kilpela et al. U.S. Pat. Nos. 5,415,658 and 5,649,927. Also, the Dall-Miles crimp is a crushable crimp having a pair of bores extending therethrough to receive cable or wire and to retain them when the crimp is crushed.

It is desirable to maximize the capability of crimps to be retained in a single, predetermined position against a bone after it has been applied to one or more cables, to hold the cable and crimp under tension in a predetermined position. It is also desirable for such a crimp to collapse with a decreased tool force, while at the same time retaining a highly efficient "hold" of the crimp on the cable. Such crimps also desirably retain a low profile as they rest on the bone, in a manner described in the previously cited U.S. Pat. No. 5,649,927.

By this invention, a crimp is provided which exhibits the above advantages, for more effective surgical utility.

DESCRIPTION OF THE INVENTION

In accordance with this invention, a malleable metal crimp is provided for securing a plurality of wire or cable portions together, typically for securing bones together in a desired position as part of orthopedic surgery. The crimp defines a pair of separate, parallel bores extending through the crimp, to each receive a wire or cable portion. The crimp has a pair of opposed ends which each define a pair of circumferentially-spaced, outwardly projecting flanges which are respectively positioned on opposite sides of the crimp. Thus, the flanges may rest against the bone while providing spacing for jaws of crimping pliers between a central portion of the crimp and the bone. Thus, such a crimp may be tightly secured to tensioned cable with crushing to secure the cable (or wire) under the desired tension, without significant loss of tension after the crimping pliers are withdrawn.

Preferably, the flanges of the crimp each define at least one pointed tooth for engaging a bone, to resist slippage of the crimp relative to the bone. Typically, four pointed teeth are provided, one adjacent to each corner of the crimp.

It is also preferred for the crimp to carry a central, external groove, formed on the crimp parallel to the bores and between the crimp ends for the purpose of facilitating collapse of the crimp. Such grooves can allow a significantly decreased tool force required to successfully collapse the crimp and to secure it onto the cable or wire. Additionally, such grooves can provide more efficient holding of the cable or wire by the crimp after it has been collapsed.

Preferably, the flanges of the crimp each define a circumferential angle about the nearest bore to each respective flange of about 30 to 90 degrees. Also, the respective centers of the flanges (the point within the flange which, on balance, is farthest spaced from the edges of the flange) are each preferably positioned to one side of a plane which encloses both longitudinal axes of the bores. In other words, from an end view of the crimp, the flanges appear to be directed downwardly, toward the bone on which the flange rests in the typical position of use of the flange.

Additionally, special crimping pliers may be used for crushing the crimp of this invention and applying it into gripping relation on cable or wire. Such crimping pliers comprise a pivotally connected pair of handles, each of the handles connecting to one of a pair of interacting jaw portions at the end of each of the handles, to form a pliers jaw for crushing cable/wire crimps which are positioned between the interacting jaw portions. One or both of the jaw portions may be pivotally connected to the handles, in a known configuration for the design of crimping pliers.

By this invention, one of the jaw portions comprises a pair of sidewalls and spaced, crimp retaining prongs, which sidewalls define a crimp space between the retaining prongs. The other of the jaw portions defines a single crimp gripping and crushing prong, which is positioned to move toward the crimp space as the jaw portions are pivoted to a closed, crimp-crushing position. Specifically, the spacing of the pair of crimp retaining prongs and dimensions of the single crimp gripping and crushing prong may be such that the crimp gripping and crushing prongs can enter into the crimp space when the crimping jaws are closed.

It is preferable for the crimp-retaining prongs to define outer walls of a pair of transversely extending crimp retaining troughs, although, if desired, the pair of troughs may comprise sections of a single trough as an equivalent structure. The crimp space is preferably defined by a longitudinally extending trough in one of the jaw portions, which longitudinally extending trough extends rearwardly along the jaw portion beyond the crimp space, and which has a floor that is deeper than the floor or floors of the transversely extending crimp retaining troughs. This longitudinally extending trough may be sized to receive the other jaw, including the single, crimping and crushing prong or projection. Specifically, this other jaw, which is typically the upper jaw of the crimping pliers, may comprise a piece of a single plate which, in turn, defines the single crimp gripping and crushing prong or projection.

Thus a double bore crimp may be provided having a firmly retained position on a bone, which retention is resistant to lateral movement because of the presence of pointed teeth that engage the bone to resist slippage of the crimp. Furthermore, the crimp may be more easily crushed with lower crushing force exerted by crimping pliers or the like, while retention of wires and/or cables inserted in the bores may remain very strong and even may be improved.

DESCRIPTION OF THE DRAWINGS

In the drawings, FIG. 1 is an elevational view, taken partly in transverse section, of a crimp in accordance with this invention, shown to be seated on a bone;

FIG. 2 is a sectional view taken along line 2—2 of FIG. 1;

FIG. 3 is a sectional view taken along line 3—3 of FIG. 1;

FIG. 4 is an elevational view, taken partly in section, along line 4—4 of FIG. 1;

FIG. 5 is a plan view of crimping pliers which have been adapted for use with the crimp of this invention;

FIG. 6 is an enlarged, perspective view of the crimp-crushing jaws of the pliers of FIG. 5;

FIG. 7 is an enlarged perspective view of the crimping jaws of FIG. 6, shown to be holding the crimp of FIG. 1;

DESCRIPTION OF SPECIFIC EMBODIMENTS

Figure 8:
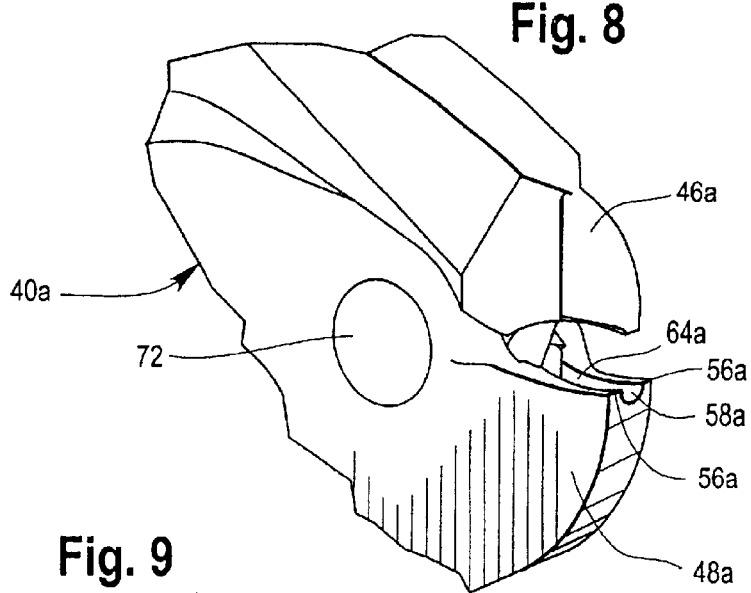
FIG. 8 is a fragmentary enlarged perspective view of another embodiment of the crimping jaws of this invention.

Referring to FIGS. 1 through 4, malleable metal crimp 10 is shown, being made of a conventional crimp alloy suitable for the purpose.

As shown, crimp 10 has a crimp body 12 that defines a pair of separate, parallel bores 14, 16 extending through the crimp. Each of bores 14, 16 are for the purpose of receiving a portion of a wire or cable, and for retaining such wire or cable portion as the crimp is collapsed so that the bores 14, 16 collapse inwardly about the wire or cable portions and retain them with firm retention.

Crimp 10 also defines a pair of opposed ends 18, 20 through which the respective bores 14, 16 extend. Ends 18, 20 each define a pair of circumferentially-spaced, outwardly projecting flanges 22, 24 on one end and identical flanges 22a, 24a on the other end. Flanges 22, 22a, and 24, 24a are respectively positioned on opposite sides of the crimp (and opposite ends of bores 14, 16), to permit the respective flanges to rest against a bone B while providing spacing 26 for crimping jaws between a central portion of the crimp and the bone.

Each of flanges 22, 22a, 24, 24a defines a pointed tooth 28 for engaging bone B to resist slippage of the crimp relative to the bone. Teeth 28 can dig into the bone surface to a small degree, when held against the bone under tension of cable or wire passing through bores 14, 16, to eliminate the possibility of such lateral slippage along the surface of bone B.

A central, external groove 30 is defined on the lower side of the crimp (in customary mode of use) as particularly shown in FIGS. 1 and 3. Groove 30 facilitates the collapse of crimp 10 in the jaws of crimping pliers, with lower crushing forces being required. Also, the opposite side of crimp 10 may carry a shallower groove 32 as shown in particularly FIGS. 1 and 2, to further facilitate crimp collapse.

Each of flanges 22, 22a, 24, 24a preferably defines a circumferential angle about the nearest of the respective bores 14, 16 of about 30 degrees to 90 degrees for example as shown by angle 34 in FIG. 1, the angle being measured from ends of the outermost periphery of each flange. Upper edge 36 of each flange (as illustrated with respect to flange 24) preferably angles downwardly as shown from the upper edge of crimp 10, so as to keep the upstanding height of the crimp above bone B to a minimum.

Also, as illustrated in FIG. 1, the respective centers 38 of each of the flanges (as illustrated in flange 22) are each positioned to one side of a plane enclosing both longitudinal axes of bores 14, 16. It can be seen that such a plane extends above each of the centers 38 of the respective flanges 22, 22a, 24, 24a.

Thus, by this invention, an improved crimp is provided which carries preferably two lumens for receiving surgical cable or wires. The presence of the two lumens make proper tensioning of the surgical cable wrap around the bone easier, and also facilitates cutting off of the surgical cable or wire adjacent to the crimp after the crimp has been crushed, for retaining of the surgical cable or wire in a desired surgical wrap around a bone or the like. The nature of the particular wrap of surgical cable or wire incorporating the crimp of this invention may be as chosen by the surgeon and will generally represent conventional techniques.

Figure 12:
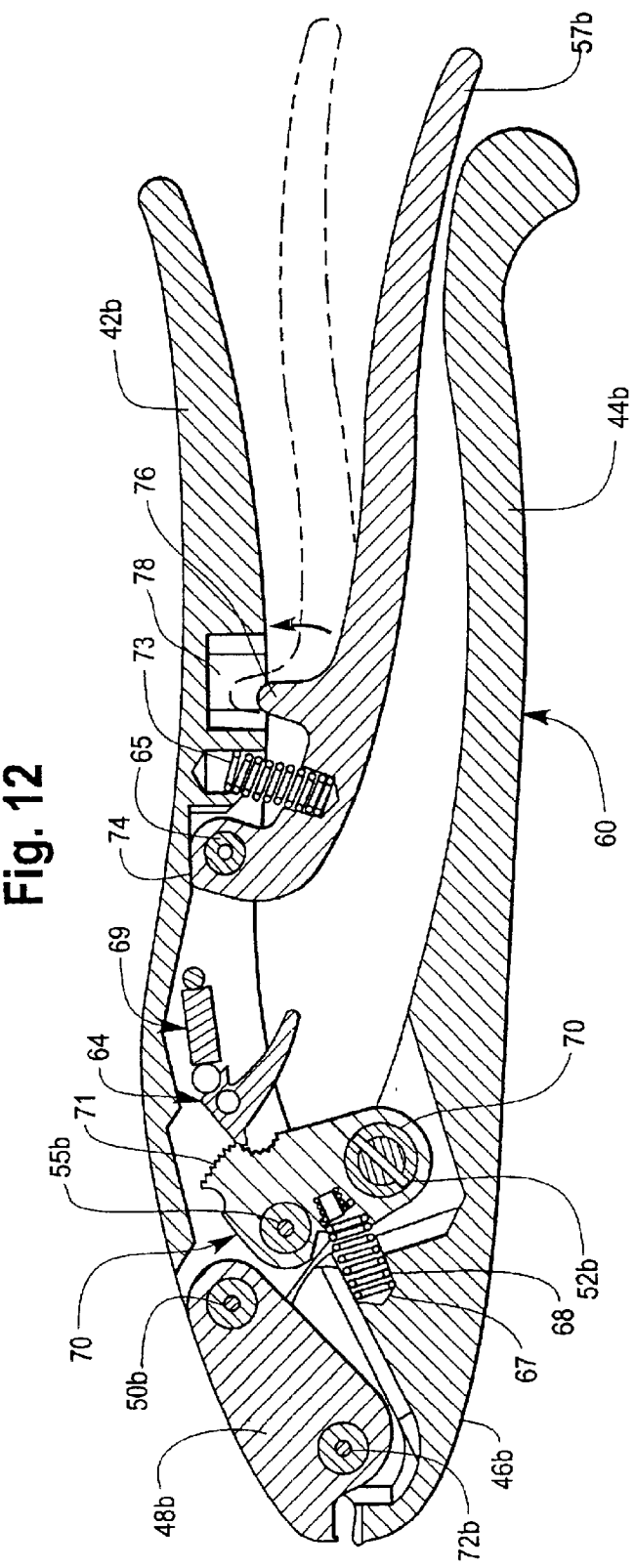
FIG. 12 is a longitudinal sectional view of crimping pliers of this invention.

Referring now to FIGS. 5 through 7 and 12, crimping pliers 40 are shown comprising a pivotally connected pair of handles 42, 44, with each of the handles connecting to a pair of interacting jaw portions 46, 48. It can be seen that handle 42 connects with jaw portion 48 through pivots 50, 55, while jaw portion 48 connects with jaw portion 46 through pivot 72, and is integral with handle 44 (FIG. 12). The respective handles 42, 44 are connected together by pivot 52.

Jaw portion 48 comprises a pair of laterally spaced crimp retaining prongs 56 defining a crimp space 58 between retaining prongs 56, plus a recess 60 for retaining crimp 10 as particularly illustrated in FIG. 7. Jaw portion 46, in turn, defines a single crimp gripping and crushing projection 62, which is positioned to move toward crimp space 58 as the jaw portions 46, 48 are pivoted to a closed, crimp crushing position by the squeezing of handles 42, 44. It can be seen that the laterally spaced crimp retaining portions 56 are spaced a sufficient distance to permit crimp gripping and crushing projection 62 to fit between them if jaws 54 are sufficiently closed by operation of handles 42, 44. Crimp retaining prongs 56 also define outer walls of the respective crimp retaining troughs 60, which may be considered a single crimp retaining trough if desired.

Also, crimp space 58 is seen in FIG. 6 to be also defined by a longitudinally extending trough 64 in jaw portion 48. The width of trough 64 is also sufficient to receive jaw 46, which comprises a plate 62 of uniform, opposed, flat surfaces 66, which are spaced to fit into longitudinal trough 64 and which define crimp gripping and crushing plate or projection 62.

Turning to FIG. 7, crimp 10 is shown to be carried in jaws 54 of the pliers of FIGS. 5 and 6, a lower edge of crimp 10 being retained by crimp retaining prongs 56 so that the lower side of crimp 10 resides in transverse troughs 60. The other side of crimp 10 is held by gripping and crushing projection 62, the position of jaws 54 and crimp 10 in FIG. 7 being that prior to crushing of the crimp.

In a typical surgical procedure, cable passes through bores 12, 14, extending out of both ends of the crimp bores and being involved in a wrap around a bone of a patient or the like as part of orthopedic surgery. The cables are pulled tight, so that crimp 10 is driven into contact with bone B upon which it resides (FIGS. 1 and 4), following which the crimping action is exerted on crimp 10 by pliers 40, while the cable remains under tension. Thus, the cable and crimp are forced together into a unitary system where the cable cannot slip out of or along the crimp, and crimp 40 is affixed on bone B. Then, free ends of the cables may be cut away from one end or the other of bores 12, 14.

FIG. 5 also shows a pivoted, auxiliary handle 57, which is provided to assist those with smaller hands to close the crimping pliers under pressure. Auxiliary handle 57 is attached to pliers handle 42 through pivot 59 so that auxiliary handle 57 can pivot through a limited range as shown. Clockwise pivoting as shown in FIG. 5 is limited by an abutment 57a, which presses against handle 42 when auxiliary handle 57 is in the extreme clockwise position shown in the broken lines.

Thus, a small handed person has less of a reach when he or she uses the auxiliary handle 57a to initiate closing of the crimp pliers against the resistance which may be afforded by a crimp. Then, when the crimp pliers handles have closed further, the user may grasp handle 42 to complete the crimping process.

In FIG. 5, auxiliary handle 57 is of U-shaped cross section so that it can fit around handle 42 in an extreme counterclockwise rotational position, so as not to interfere with the final closing of crimping pliers 40.

Figure 9:
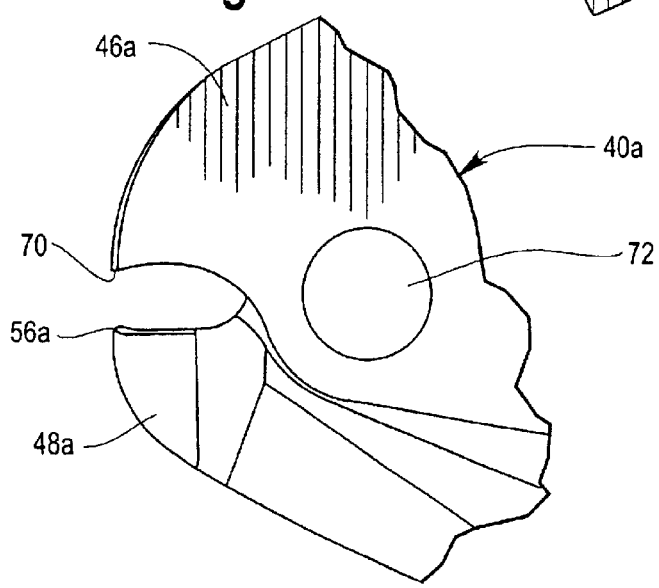
FIG. 9 is a fragmentary, side elevational view of the crimping jaws of FIG. 8.
Figure 10:
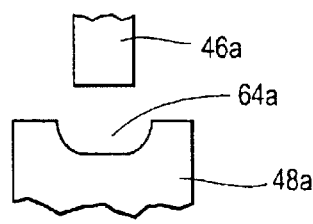
FIG. 10 is a fragmentary, schematic, front elevational view of the crimping pliers of FIG. 8, showing the interaction between the two jaws.

Referring to FIGS. 8–10, portions of the jaws of crimping pliers 40a are shown, the crimping pliers being otherwise similar to the previously described crimping pliers 40 except as otherwise described herein. In the embodiment the respective jaw portions 46a, 48a are shown with a more rounded design than their counterparts in the previous embodiment, but the jaws are basically of a structure and function similar to the previous embodiment. Crimp retaining prongs 56a in this embodiment are less pronounced than in the previous embodiment, but still present to retain a crimp in position for the crimping procedure in a manner similar to that of the previous embodiment. Upper jaw 46a also defines a crimp retaining prong 70 to retain an upper edge of a crimp within the jaws.

Crimp space 58a is, like the previous embodiment, defined by a longitudinally extending trough 64a as in the previous embodiment.

Jaws 46a, 48a pivot into open and closed position about pivot 72, for a simplification of the pivoting system from the previous embodiment.

Turning to FIG. 10, it can be seen that jaw 46a is capable of fitting into longitudinally extending trough 64a (and the included crimp space 58a) for complete, strong crimping action.

Figure 11:
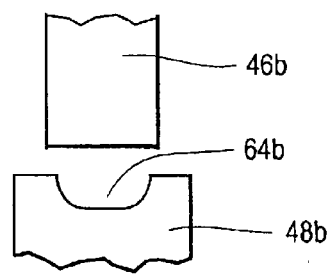
FIG. 11 is a similar front elevational view of a modification of the crimping jaws from that shown in FIGS. 8–10, with the crimping pliers being otherwise similar to those figures.

Alternatively, as shown in FIG. 11, another design of jaw which is otherwise similar to that disclosed above may be provided where upper jaw 46b is too wide to fit into longitudinal trough 64b as defined in lower jaw 48b. Either of the above designs of FIGS. 10 and 11 can be effective in the various embodiments of crimping pliers in accordance with this invention.

Referring to FIG. 12, a design for the pliers of this invention is shown having jaws similar to the embodiment of FIGS. 8–10 but otherwise applicable to the embodiment of FIG. 5, and showing a new embodiment 57b of auxiliary handle similar to handle 57, while showing the jaw opening and closing mechanism which is applicable to all previous embodiments. Pliers 60 comprises handles 42b, 44b as in the previous embodiments, which handles are pivotally connected to jaw portion 48b. Jaw portion 46b is integral with handle 44b as in the embodiment of FIG. 5. Pivots 50b, 52b, 55b and 72b are positioned in similar manner to the corresponding pivots of the FIG. 5 embodiment, for similar purpose. Crimping pliers 60 carry an eccentric ratchet member 70 which connects to pivot 55b, being biased by small and large compression springs 67, 68 and carrying a ratchet 71 which is engaged by pawl 64, biased by spring 69.

The pawl and ratchet system 64, 70 requires complete closing of handles 42b, 44, when closing is initiated, in order to assure that complete crimping of the crimp takes place. Upon complete closing, the pawl and ratchet disengage to permit opening of the handles, which system is known in the prior art.

Auxiliary handle 57b is present for a purpose similar to auxiliary handle 57 of FIG. 5, with handle 57b being of a somewhat different design. As shown, handle 57b is pivotally attached to handle 42b at pivot 65, being biased inwardly toward handle 44b by means of spring 73 to a maximum range as shown, where flat surfaces 74 abut each other to prevent further clockwise rotation of handle 57b.

Projection 76 fits into aperture 78 as auxiliary handle 57b rotates toward handle 44b, to provide lateral strength and prevention of lateral motion between the handles in a direction perpendicular to the pivotal plane of motion shown.

The above has been offered for illustrative purposes only and is not intended to limit the scope of the invention of this application, which is as defined in the claims below.

What is claimed is:

1. Crimping pliers which comprise a pivotally connected pair of handles, each of said handles connecting to one of a pair of interacting jaw portions at an end of each of said handles to form a pliers jaw for crushing cable/wire crimps positioned between said interacting jaw portions, said pliers carrying an auxiliary handle of substantially similar length to handles of said pair, said auxiliary handle being pivotally mounted on one of said handles of said pair to permit limited-range, pivotal movement of said auxiliary handle to a position between the other handles, to facilitate closing of said crimping pliers for crimping action by a person with a small hand, in which said auxiliary handle is spring biased to pivot away to the extreme of its limited pivotal range from the handle to which it is pivotally connected.

2. The crimping pliers of claim 1 in which said auxiliary handle is of U-shaped cross section so that it can fit around said one handle of said pair in an extreme rotational position, so as not to interfere with the final closing of said crimping pliers.

3. Crimping pliers which comprise:

a first handle and a second handle;

said first handle connecting to a first jaw portion at an end of said first handle;

said second handle connecting to a second jaw portion at an end of said second handle;

said first jaw portion and second jaw portion being interacting to form a pliers jaw for crushing cable/wire crimps positioned between said interacting jaw portions;

said first jaw portion comprising a first outer side wall and a second outer side wall laterally spaced from said first outer side wall, said first and second side walls defining a single, open crimp space therebetween, said crimp space having a major dimension extending in a direction longitudinal to said first and second outer side walls;

said first side wall having a first crimp-retaining prong;

said second side wall having a second crimp-retaining prong;

said second jaw portion comprising a single, rigid, metal crimp gripping and crushing plate, which plate is operative to move toward said crimp space between said first wall and said second wall as the interacting jaw portions are pivoted to a closed, crimp crushing position, with an edge of said plate engaging said crimp.

4. The crimping pliers of claim 3 in which said crimp retaining prongs define part of the outer walls of a pair of transversely extending crimp retaining troughs.

5. The crimping pliers of claim 3 in which an auxiliary handle is pivotally mounted on one of said first and second handles to permit limited-range, pivotal movement of said auxiliary handle to a position between the first and second handles, to facilitate closing of said crimping pliers for crimping action by a person with a small hand.

6. The crimping pliers of claim 5 in which said auxiliary handle is of U-shaped cross section so that it can fit around said one of said first and second handles of said pair in an extreme rotational position, so as not to interfere with the final closing of said crimping pliers.

7. The crimping pliers of claim 3 in which said crimp retaining prongs define part of the outer walls of a pair of transversely extending crimp retaining troughs, and further in which an auxiliary handle is pivotally mounted on one of said first and second handles to permit limited-range, pivotal movement of said auxiliary handle to a position between the first and second handles, to facilitate closing of said crimping pliers for crimping action by a person with a small hand.

8. The crimping pliers of claim 7 in which said auxiliary handle is spring biased to pivot away to the extreme of its limited pivotal range from the handle to which it is pivotally connected.

9. A crimping pliers which carries a crimp, which pliers and crimp comprise:
   a first handle and second handle;
   said first handle connecting to a first jaw portion at an end of said first handle;
   said second handle connecting to a second jaw portion at an end of said second handle;
   said first jaw portion and second jaw portion interacting to form a pliers jaw for crushing a cable/wire crimp which is positioned between said interacting jaw portions;
   a cable/wire crimp being so positioned between said interacting jaw portions;
   said first jaw portion comprising a first outer side wall and a second outer side wall laterally spaced from said first wall, said first and second side walls defining a single, open crimp space therebetween;
   said first wall having a first crimp-retaining prong;
   said second wall having a second crimp-retaining prong;
   said second jaw portion comprising a single, rigid, metal crimp gripping and crushing projection which is operative to move toward said crimp space between said first wall and said second wall as the interacting jaw portions are pivoted to a closed, crimp-crushing position.

10. The crimping pliers of claim 9 in which an auxiliary handle is pivotally mounted on one of said handles to permit limited-range pivotal movement of said auxiliary handle to a position between the other handles, to facilitate closing of said crimping pliers for crimping action by a person with a small hand.

11. The crimping pliers of claim 10 in which said auxiliary handle is of u-shaped cross section so that it can fit around said one of said handles of said pair in an extreme rotational position, so as not to interfere with the final closing of said crimping pliers.

12. The crimping pliers of claim 10 in which said auxiliary handle is spring biased to pivot away to the extreme of its limited pivotal range from the handle to which it is pivotally connected.

13. The crimping pliers of claim 9 in which said second jaw portion comprises a plate, with an edge of said plate engaging said crimp.

* * * * *